(12) United States Patent
Keating et al.

(10) Patent No.: US 9,492,072 B2
(45) Date of Patent: Nov. 15, 2016

(54) LAPAROSCOPIC SURGICAL DEVICE

(75) Inventors: Ronan Keating, Galway (IE); Gerard Rabbitte, Galway (IE); Barry Russell, Kildare (IE); Suzanne O'Rorke, Galway (IE)

(73) Assignee: NEOSURGICAL LIMITED, Galway (IE)

( * ) Notice: Subject to any disclaimer, the term of this patent is extended or adjusted under 35 U.S.C. 154(b) by 742 days.

(21) Appl. No.: 13/638,927

(22) PCT Filed: Mar. 18, 2011

(86) PCT No.: PCT/EP2011/054161
§ 371 (c)(1),
(2), (4) Date: Nov. 20, 2012

(87) PCT Pub. No.: WO2011/120828
PCT Pub. Date: Oct. 6, 2011

(65) Prior Publication Data
US 2013/0066155 A1 Mar. 14, 2013

Related U.S. Application Data

(60) Provisional application No. 61/323,369, filed on Apr. 13, 2010.

(30) Foreign Application Priority Data

Mar. 31, 2010 (GB) .................................. 1005452.6

(51) Int. Cl.
*A61B 1/32* (2006.01)
*A61B 17/02* (2006.01)
*A61B 17/04* (2006.01)

(52) U.S. Cl.
CPC .................. *A61B 1/32* (2013.01); *A61B 17/02* (2013.01); *A61B 17/0218* (2013.01); *A61B 2017/0225* (2013.01); *A61B 2017/0464* (2013.01)

(58) Field of Classification Search
CPC .............. A61B 17/02; A61B 17/0218; A61B 2017/0225; A61B 17/3421; A61B 17/3423; A61B 17/3431
USPC .................................................. 600/201–246
See application file for complete search history.

(56) References Cited

U.S. PATENT DOCUMENTS 5,242,456 A 9/1993 Nash
5,582,577 A 12/1996 Lund et al.
(Continued)

FOREIGN PATENT DOCUMENTS

DE 19841652 A1 3/2000
EP 2123227 A1 11/2009
(Continued)

*Primary Examiner* — Ellen C Hammond
*Assistant Examiner* — Christina Negrellirodrigue
(74) *Attorney, Agent, or Firm* — Schwabe, Williamson & Wyatt, P.C.

(57) ABSTRACT

A laparoscopic surgical device comprising an anchor element comprising a pair of jaws defining a mouth within which at least a portion of an organ or tissue may be grasped is described. The jaws are biased towards one another so as to normally adopt a closed configuration. The anchor element is coupled to a support member, the support member being moveable about the anchor element. The device is dimensioned to be operably passed fully through a trocar into the abdominal cavity wherein it may be manipulated by a surgeon or other operator to grasp the desired target organ or tissue.

57 Claims, 10 Drawing Sheets

(56) References Cited

U.S. PATENT DOCUMENTS

| | | | |
|---|---|---|---|
| 6,123,667 A * | 9/2000 | Poff | A61B 17/0218 600/201 |
| 6,142,935 A * | 11/2000 | Flom | A61B 17/0293 600/206 |
| 7,070,558 B2 * | 7/2006 | Gellman et al. | 600/37 |
| 7,112,172 B2 * | 9/2006 | Orban, III | A61B 17/0218 600/204 |
| 7,892,244 B2 * | 2/2011 | Monassevitch et al. | 606/151 |
| 2009/0137877 A1 * | 5/2009 | Minnelli | A61B 17/0218 600/204 |
| 2009/0198107 A1 | 8/2009 | Park et al. | |
| 2010/0174150 A1 * | 7/2010 | Park et al. | 600/218 |

FOREIGN PATENT DOCUMENTS

| | | |
|---|---|---|
| WO | 93/09721 A1 | 5/1993 |
| WO | 03/096907 A1 | 11/2003 |
| WO | 2008/045940 A2 | 4/2008 |

* cited by examiner

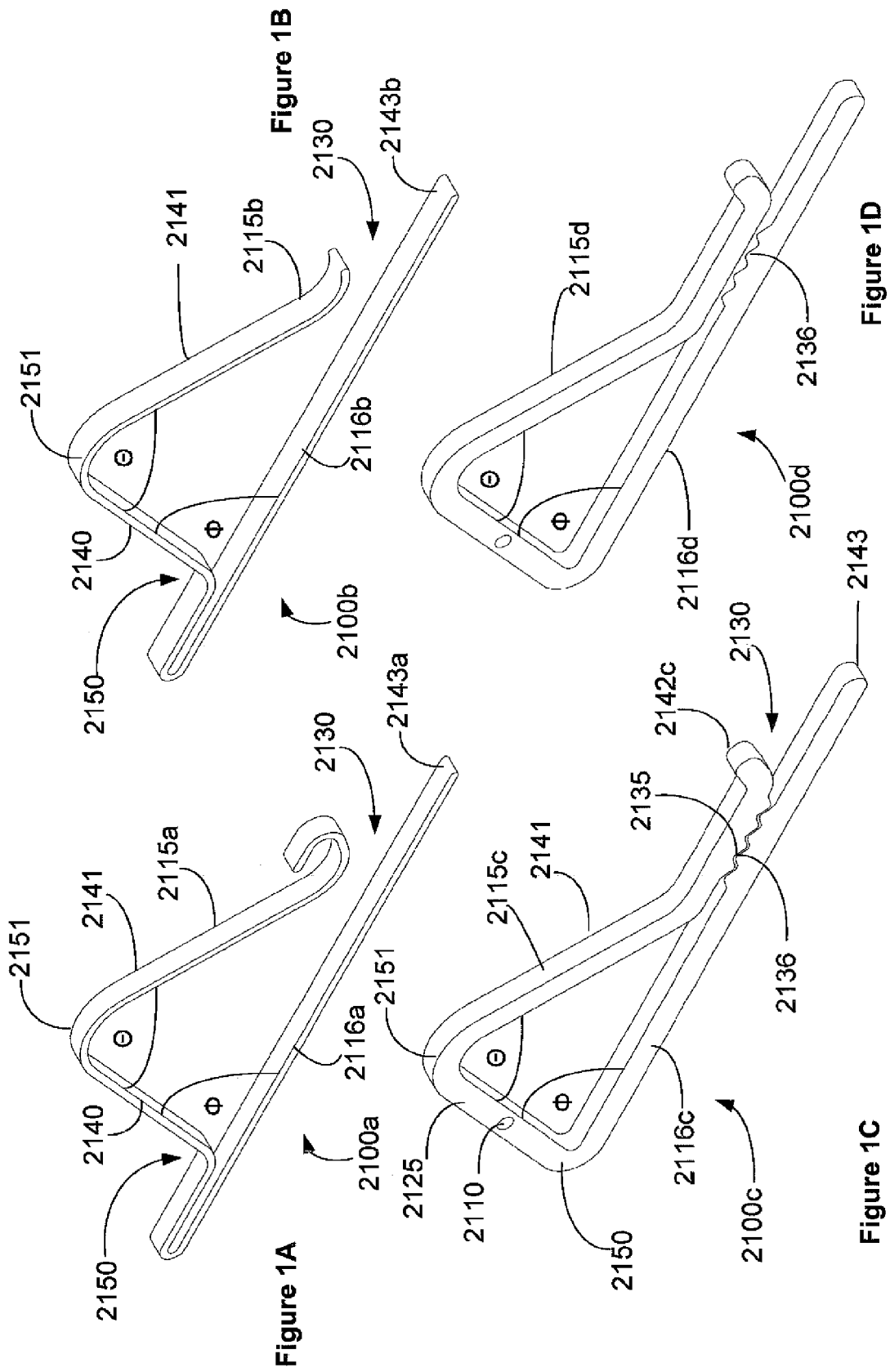

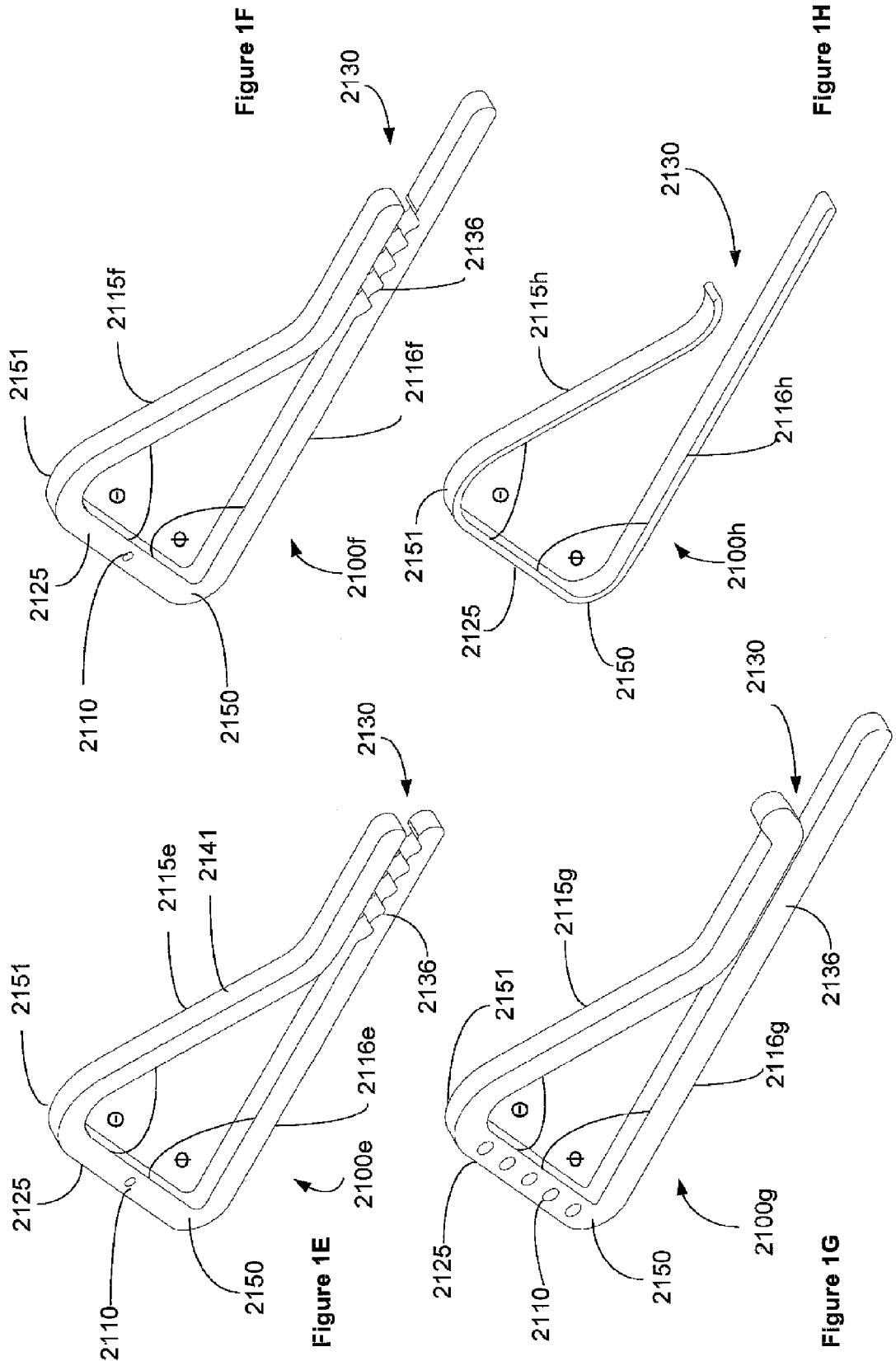

LAPAROSCOPIC SURGICAL DEVICE

FIELD OF THE INVENTION

The present invention relates to traditional laparoscopic surgery and the emerging technique referred to as single incision laparoscopy. The invention more particularly relates to devices, preferably retraction devices, for use in laparoscopic surgery and single incision surgery. The invention also relates to method of laparoscopic surgery and single incision surgery.

BACKGROUND

Laparoscopic surgery which is also known as keyhole surgery or minimally invasive surgery (MIS) is a surgical technique in which operations in the abdomen are performed through small incisions provided in the abdomen wall. The incisions are typically of the order of 0.5-2.5 cm and provide the surgeon with access to the interior cavity for performing the necessary surgical operation. The cavity is typically inflated with carbon dioxide, to increase the volume of the cavity so as to provide the necessary working and viewing space for the surgeon.

The surgical instruments are inserted into the abdominal cavity through a cannula or trocar located within the incisions in the cavity wall. For laparoscopic surgery, each operation typically requires a minimum number of such incisions to enable the use of a sufficient number of instruments as determined by the surgeon. The control of the instruments is effected outside the body cavity. By using such minimally invasive surgical techniques as opposed to earlier open surgical procedures there are a number of advantages including the fact that the smaller incisions used amongst other factors reduces the pain of the operation and shortens recovery times for the patients. There are many factors contributing to reduced patient morbidities with minimally invasive surgery over open surgery which make this an increasingly attractive option for patient and surgeon. For this reason there is a more recent push towards even less invasive laparoscopic approaches. There are various names and acronyms attached to this emerging technique of surgery including Single Incision Laparoscopic surgery (SILS) and Lapro-Endoscopic Single-Site Surgery (LESS) amongst many others. Fundamentally, the aim is to operate from one site, typically at the umbilicus, thereby eliminating the extra ports and improving cosmesis for the patient. However, this approach introduces additional constraints on the operator over the traditional laparoscopic approach and is likely to require new flexible and accessible instruments to complete the surgical procedure efficiently.

As the surgery is completed through a relatively small number of small diameter access points to the interior cavity, it is preferable to have only one operator of the instrumentation within the cavity. However due to the number of instruments that may need to be operated concurrently, there is often a requirement for two or more persons to operate the instruments concurrently, which can be a nuisance in that each of the multiple persons add cost and potentially increases the risk of a complication occurring. The addition of extra personnel is a challenge for private practices that may not have the human resources to meet this need. Whether in a public or private hospital setting, the majority of surgeons would prefer to be in control of their set up and the operating environment.

Furthermore, the site of the surgery is often occluded by another organ that needs to be moved out of the field of view to allow access to the surgery site. In the context of traditional open surgery where access to the operating site is more open, this can be easily achieved by the surgeons hand or an assistants hand or a simple retraction device held in place by the operator's hand. This is often considered a conventional step in the operation. However with laparoscopic surgery, while the moving of occluding organs is still necessary, it is more difficult to achieve and has typically been achieved in one of two ways, both of which utilise retraction devices.

Known retraction devices work on the principle of holding up the target organ from outside the abdominal cavity. They are a mix of single patient use (SPU) and reusable devices depending on the manufacturer. Typically, a metal shaft is inserted via a 10/12 mm or 5 mm port and has various applicator end section designs depending on the manufacturer and model. These can for example be dimensioned to resemble finger type designs, or a simple wedge shape. Some of these designs are of metal construct but there are a number of inflatable types also available. These end applicator sections are designed and constructed in many different ways but essentially they all perform a similar function in lifting the target organ. This target organ will depend on the actual operation being completed but in the context of surgery in the area of the gastroesophageal junction and surrounding structures the left lobe of the liver is typically required to be lifted out of the field of view. They are advanced under the target organ, for example the liver, which is then leveraged up and out of the field of view using a rigid lever. The device is then held in position by an assistant or some devices are fixed to an external support frame which acts as an aid to fix it into position. In all arrangements the retraction device is secured from the outside and most designs require a dedicated port throughout usage.

Another common retraction method is applied to the right side of the liver. Typically this method is used to grasp, retract and orientate the gallbladder and the attached right liver lobe in to a position that provides a 'critical view' of the key structures at the root of the gallbladder. This procedure is known as the Laparoscopic Cholecystectomy. The typical set up for this procedure requires 4 ports, one of which is dedicated to the retraction of the gallbladder and right liver lobe.

The use of dedicated ports suffers in that an additional incision is required, and as will be appreciated from above, there is a desire in laparoscopic surgery to keep the number of incisions to a minimum. There is also a cost disadvantage of having to employ an additional port. Furthermore the maintaining of the retraction device in situ using a person requires that person to maintain a static hold for the entire procedure or certainly over prolonged periods of time causing fatigue. Fatigue usually leads to movement and in most cases there is a lack of operator control from the outset as they are relying on an assistant. Other device types require the assembly of an external fixation scaffolding around the operating table so as they can be fixed to it for the duration of the procedure and this can occupy valuable space and hinder the surgeon in his performance of the surgery. They are also reusable and require sterilisation and maintenance.

Therefore there are a number of problems associated with existing retraction devices and their methods of use. There is also a distinct shortage of solutions to deal with emerging techniques such as the single incision surgery and all of its associated procedures including but not limited to Laparoscopic Cholecystectomy, Laparoscopic Gastric Banding and Bypass, and Laparoscopic Nissen Fundoplication. Traditional laparoscopic approaches also offer challenging retraction in operations such as, but not restricted to, laparoscopic colon procedures. During this procedure the small bowel typically has to be maintained/retracted in a position out of the field of view of the target large bowel or colon. Therefore both approaches, namely, traditional laparoscopic and single incision surgeries, offer many retraction difficulties for the operator/surgeon. The emergence of the single incision approach leads to increased difficulties as there are even more limiting factors due the position of the single incision and the operating difficulties this presents to the surgeon.

SUMMARY

These and other problems are addressed in accordance with the present teaching by provision of a laparoscopic surgical device. There is also provided a method for providing access to surgical sites within the abdomen that would otherwise be occluded by other organs.

In a first arrangement a surgical device comprises an anchor element coupled to a support member. The anchor element is provided having a pair of jaws that are biased towards one another so as to normally adopt a closed configuration.

The device is dimensioned to be operably passed fully through a trocar into the abdominal cavity wherein it may be manipulated by a surgeon or other operator to effect a hold on a desired target organ. On location of the device relative to the organ and on retention of at least a portion of the organ within the jaws of the anchor element, movement of the support member relative to the anchor element will effect a corresponding movement of the retained organ. On reaching a desired location, the support member can be secured to maintain this position of the moved or retracted organ so as to facilitate surgery. Once the surgery has been completed, the organ may be allowed to return to its normal position within the abdominal cavity.

At least one of the jaws is desirably pivotable relative to the other of the jaws to allow for movement of the jaws away from one another to facilitate the presentation of an organ into a mouth region of the grasper. As the jaws are naturally biased towards one another, this pivoting requires provision of an external force so as to effect a separation of the jaws away from one another.

The level of amount of the bias force which acts to maintain the jaws towards one another is related to the intended use of the grasper, specifically the nature of the organ/tissue which is to be retained by the anchor element. Desirably the force is sufficient to ensure that once located within the jaws, the biasing of the jaws towards one another will effect a retention of the organ/tissue therein without any slippage. At the same time the force cannot be so great as to effect a cutting or damaging of the organ/tissue.

The anchor element defines a clasping element again comprising a first and a second jaw that are biased towards one another. In this arrangement the jaws are integral with one another and are fabricated in a shape memory material which may be copper, NiTi (nickel and titanium), or polymer based. By fabricating at least one of the first and second jaws in such a shape memory material which may deform but which will return to its normal state the jaws can be configured through a suitable shaping of the jaws to be naturally biased towards one another. In this way the jaws may be separated to allow for the location of an organ or other tissue therebetween. The construct of the jaws is such that jaws will tend to move towards one another, the movement effecting a capture or clasping of the organ/tissue therebetween. A plastic or elastic material may also be used to fabricate this arrangement.

Such a device may be used in combination with a suture or other fastening means to effect a movement of the clasped organ or tissue from its normal resting position to an operational site where for example access to a site normally occluded by the normal resting position is required.

Accordingly there is provided a device as claimed in claim 1 with advantageous embodiments detailed in the dependent claims thereto. Methods according to the independent method claims are also provided. Use of a device as detailed in the use claim is also provided.

These and other features of the present invention will now be described with reference to an exemplary arrangement thereof which is provided to assist in an understanding of the teaching of the invention but is not intended to be construed as limiting the invention to the exemplary arrangements which follow.

BRIEF DESCRIPTION OF THE DRAWINGS

The present invention will now be described with reference to the accompanying drawings in which:

FIG. 1 shows various configurations for a clasping device in accordance with the present teaching.

DETAILED DESCRIPTION OF THE DRAWINGS

Figure 2:
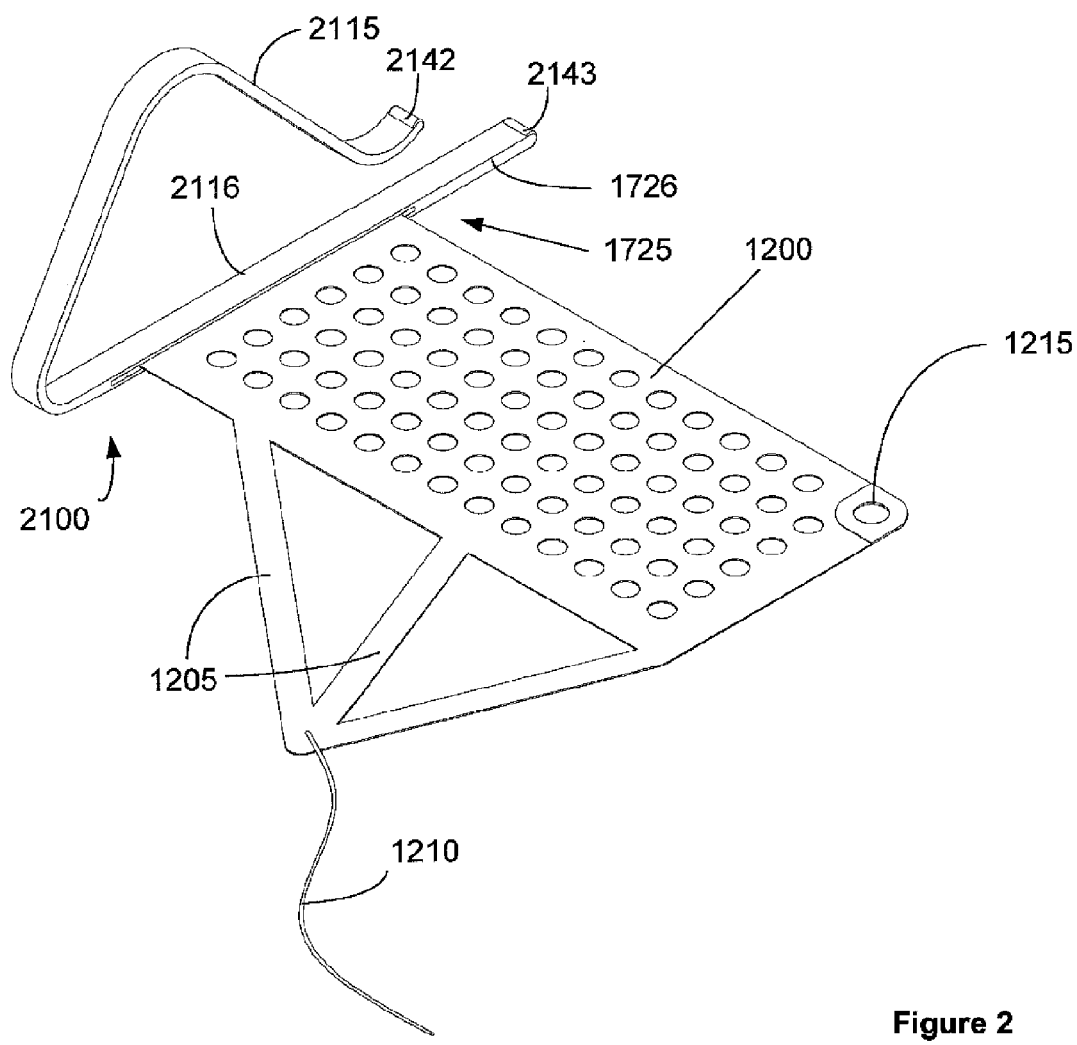
FIG. 2 shows a support member portion of a device in accordance with the present teaching incorporating a plurality of straps that may be moved relative to a main body of the support member so as to at least partially encapsulate an organ.

Exemplary arrangements of devices for laparoscopic surgery will now be described to assist in an understanding of the present teaching. Such arrangements illustrate exemplary arrangements of an anchor element coupled to a support member. It will be appreciated that the following examples are provided to assist in an understanding of the present teaching and are not to be construed as limiting the present teaching to these exemplary arrangements of different retraction devices. Furthermore where one or more features or components are described with reference to one retraction device it will be understood that such features or components could be used with other exemplary retraction devices without departing from the present teaching. Therefore it will be appreciated and understood that it is not intended to limit the present teaching to any one exemplary retraction device or components related to same.

FIGS. 1A through 1H show configurations of an anchor or clasping element component of a surgical device in accordance with the present teaching where the references "a", "b" "c" etc refer to components shown in specific views. In these views, the support member which is typically coupled to the anchor is not shown. The clasping element 2100 comprises a first 2115 and a second 2116 jaw that are biased towards one another. In these arrangements the jaws are integral with one another and are fabricated in a shape memory material such as copper-based, NiTi (nickel and titanium)-based (Nitinol), and/or polymer shape memory materials. By fabricating at least one of the first and second jaws in such a shape memory material which may deform but which will return to its normal state the jaws can be configured through a suitable shaping of the jaws to be naturally biased towards one another. In this way the jaws may be separated to allow for the location of an organ or other tissue therebetween. The construct of the jaws is such that jaws will tend to move towards one another (or one jaw will tend to move towards the other), the movement effecting a capture or clasping of the organ/tissue therebetween. In this arrangement, the jaws are spaced apart from another, the upper jaw being configured to being naturally biased toward the lower jaw or vice versa. The jaws are operably separable to allow for the location of an organ or other tissue therebetween. The first jaw 2115 comprises first 2140 and second 2141 segments angularly offset from one another. In the examples shown the first segment 2140 extends away from the second jaw 2116 and the second segments 2141 extends towards the second jaw 2116. The first jaw may comprise a third segment 2142, provided at an end portion of the second segment 2141, the third portion defining the tip of the first jaw. This tip may be provided in atraumatic or traumatic configurations.

In the configurations of FIGS. 1C through 1G, the third segment 2142 comprises a planar portion extending from the second segment, the planar portion being substantially parallel with the second jaw 2116. In the arrangements of FIGS. 1A-1D and 1G-1H, the third segment comprises a curved surface, the curved surface defining the end of the first jaw. Where the third segment comprises both a curved surface and a planar portion, the planar portion is desirably provided between the curved surface and the second segment.

The anchor or clasping element of FIG. 1 is desirably collapsible upon itself such that the upper arm 2115 may be brought into intimate contact with the lower arm 2116. This is affected by applying a force at the shoulder 2150 to effect a movement of the tip 2142 of the upper arm in a direction downwardly towards the corresponding leading edge or end portion 2143 of the lower arm 2116. In a collapsed configuration the first and second arms are substantially parallel to allow for the insertion of the device through a narrow bore trocar or cannula. By fabricating in a shape memory material, on removal of the force the arms will tend to separate and adopt their normal configuration—as shown in FIG. 1. In another configuration, application of a force anywhere along the first segment 2140 or at the apex 2151 of the first jaw 2115 will affect a collapse of the first jaw 2115 downwardly onto the second jaw 2116.

Such a clasping element may be used in combination with a suture or other fastening means to effect a movement of the clasped organ or tissue from its normal resting position to an operational site where, for example, access to a site normally occluded by the normal resting position is required. For example as shown in FIGS. 1C through 1G one or more suture apertures 2110 may be provided in a back portion 2125 of the device to provide for a coupling of the device to a suture. Multiple suture tie holes such as shown in FIG. 1G provide the benefit of increased flexibility over this area. Radiused or chamfered curved edges may be incorporated for less traumatic applications. The suture may be supplied pre tied to the anchor element. Various iterations featuring teeth on lower 2136 and/or upper 2135 jaws are shown. Features included enable easier removal of the device with tabs for suture tying. The teeth may be traumatic or atraumatic. The biasing force of the arms can be predefined to adjust a distance between the two at the mouth 2130 of the device. For example as shown in FIG. 1B, on adoption of the normal closed position, a gap 2130 is provided in the mouth region between the upper 2115*b* and lower 2116*b* arms. In contrast in FIG. 1C, the biasing force is such that on adoption of the closed position the gap 2130 is reduced to a negligible amount, the arms are in intimate contact with one another in the mouth 2130 region.

The force is a factor of the design of the angles used to separate the upper 2135 arm from the lower 2136 arm. This angle, theta, shown in FIGS. 1A-1F has a radius defining the separation between the upwardly 2140 and downwardly 2141 segments of the upper arm 2115. This angle separating the first segment 2140 from the second segment 2141 is desirably an acute interior angle. The angle phi offsetting the first segment 2140 from the second jaw 2116 is also desirably an acute interior angle. In this way, the first 2140 and second 2141 segments of the first jaw and a portion of the second jaw are arranged relative to one another to define an acute triangle. All radii can be adjusted to achieve more or less closure force depending on the application.

As shown in FIGS. 1A through 1D and FIGS. 1F through 1H, the second jaw 2116 may be configured to extend further than the first jaw 2115, such that on operable presentation of the device to an organ or tissue, the second jaw will abut against the organ or tissue prior to the first jaw.

It will be appreciated that this clamping arrangement is configured for complete deployment within the abdominal cavity and will tend to a normally closed position which on deployment will effect a clasping of the organ or tissue between the arms until actively released. While not intending to limit the device of the present teaching to any one specific set of parameters or materials it will be appreciated that for use in deployment through a trocar that such a device should have an outside diameter smaller than the bore of the trocar to allow complete passage of the device through the trocar in the collapsed configuration. The anchor could be fabricated in any one of a plurality of different materials, examples of which are metal injection moulded materials, ceramics, metals, plastics, or composites thereof. It is desirable however that at least a portion of the anchor is fabricated from a shape memory material such as Nitinol which will allow it to deform to a collapsed configuration during presentation through the trocar but which on removal of a biasing force will extend. The jaws could be symmetric with one another or could be asymmetric.

Figure 3:
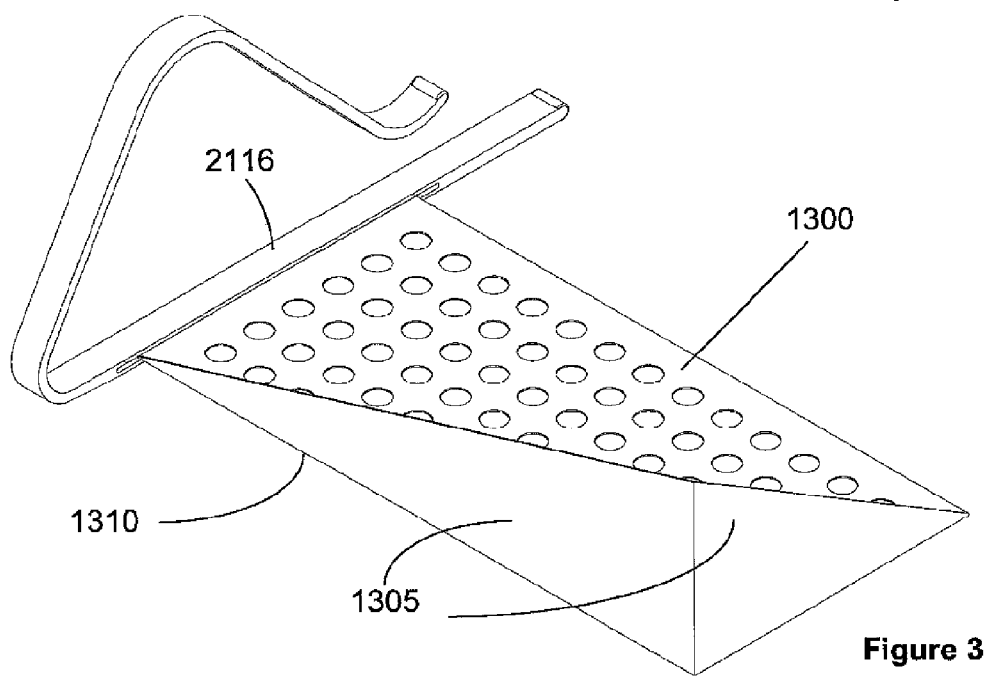
FIG. 3 shows another arrangement of a support member provided in a 3-D configuration to assist in retention of a contacted organ.

FIG. 2 shows a coupling of a clasping or anchor element 2100 as described with respect to FIG. 1 to a support member so as to provide a surgical retraction device in accordance with the present teaching. In this exemplary arrangement the support member is provided in the form of a web or mesh 1200 having one or more straps 1205 coupled thereto. The support member is flexible in this configuration so as to allow it to adopt the contours of the organ being supported. The straps 1205 are linked to a suture strand 1210. Once the mesh is placed under the organ to be retracted, the suture 1210 is passed through an eyelet 1215—shown in FIG. 2 as being on the other side of the web to the location where the suture is coupled to the straps. By then pulling the suture, the straps are configured to encircle the organ, passing around and over the organ to secure it in place. The suture can optionally be sutured to the abdominal wall or passed out through the abdominal wall. The benefit of this approach is that it provides a mechanism for preventing the organ, from slipping off the mesh or web 1200 in that the organ is retained through a tightening of the straps 1205 about the organ. The straps may be elastic to accommodate a variety of target organ geometries. The straps may be integrally formed with the material used for the body of the support member or may be formed separately and attached to the main body. Typical materials that may be employed for this specific support member, and other configurations or embodiments as described herein, include thermoplastic polyurethanes, polyesters such as PET or a silicone or silicone based elastomer. For woven embodiments mono or multifilament fibres may be used. Suitable fibres would include ultra high or high molecular weight polyethylene, other polyesters, or Kevlar fibres due to their high strength. Metallic fibres could also be used, 304 stainless steel, other stainless steels, or a shape memory material such as Nitinol which would enable a three dimensional profile to be achieved. Other, similarly performing materials could also be used. While it is not intended to limit the present teaching to any one set of parameters or values, it will be understood that in providing surgical devices that are being used to provide a surgeon with access to specific locations during surgery that it is important that the actual device is dimensioned so as to not occlude the actual view that it is trying to create. For these reasons it is desirable to form the support member as thin as possible and the use of the materials heretofore described may be advantageously employed to fabricate a support member whose wall thickness would typically range from 0.0025 mm to 1 mm and more preferably from 0.025 to 0.1 mm FIG. 3 shows a modification to such an arrangement whereby as opposed to defining a three dimensional shape web through a tightening of straps elements of the web, the web is preformed with a three dimensional shape in order to better encapsulate the organ being retracted. In the arrangement of FIG. 3, a mesh 1300 is provided having raised sides 1305 provided at an edge portion 1310 thereof, in the arrangement shown two raised sides are provided extending along the side and end of the mesh. The raised sides operably serve to provide a retention wall or pocket such that as the mesh is retracted the raised sides engage with and retain at least a portion of the liver or other organ, thereby preventing it from slipping off the mesh. This is particularly useful especially when the mesh is being retracted obliquely. A benefit of this approach over a flat or planar web is that the organ in encased more securely in the web. It will be appreciated that the shape shown here is for illustrative purposes and should not be seen as limiting the design. The shape could be stitched into the mesh from a separately formed element or the mesh may have a naturally embedded concave shape.

Figure 4:
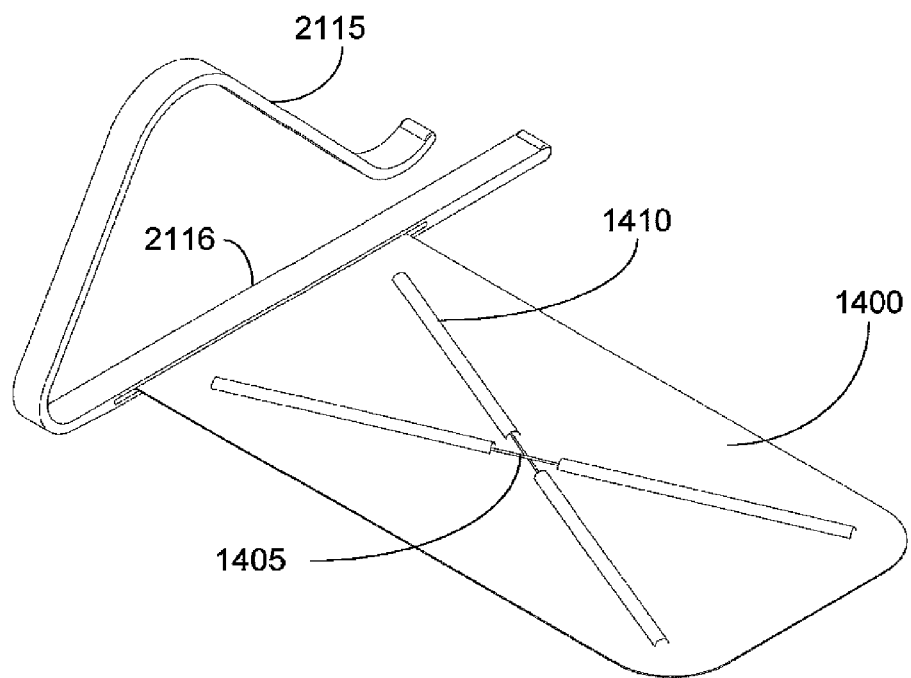
FIG. 4 shows an example of a support member incorporating superelastic shape memory material elements provided for assisted deployment of the device.

In another arrangement shown in FIG. 4 the support member is provided in the form of a web or mesh 1400 with additional nitinol supports 1405 embedded thereon or therein. In the exemplary arrangement a plurality of pockets or channels 1410 are provided on the mesh surface for receiving the supports 1405. It will be appreciated that the nitinol is an example of a shape memory material which as a result of its physical properties will tend to revert to a predefined shape on release of a force thereon. These supports 1405 ensure the mesh 1400 unfurls without the need for operator manipulation. In the exemplary arrangement illustrated, the supports are provided as two diagonal wires extending across the web 1400, but it will be appreciated that the location of the shape memory material or its configuration (for example sheet or wire) may be modified. One typical modification would be provision of a support about the perimeter or circumference of the support member to reduce the time needed to prep the device inside the body and provide an ease of use benefit. The elements could also be arranged to achieve a geometry such as that shown in FIG. 3 or to achieve a generally concave geometry also.

Figure 5:
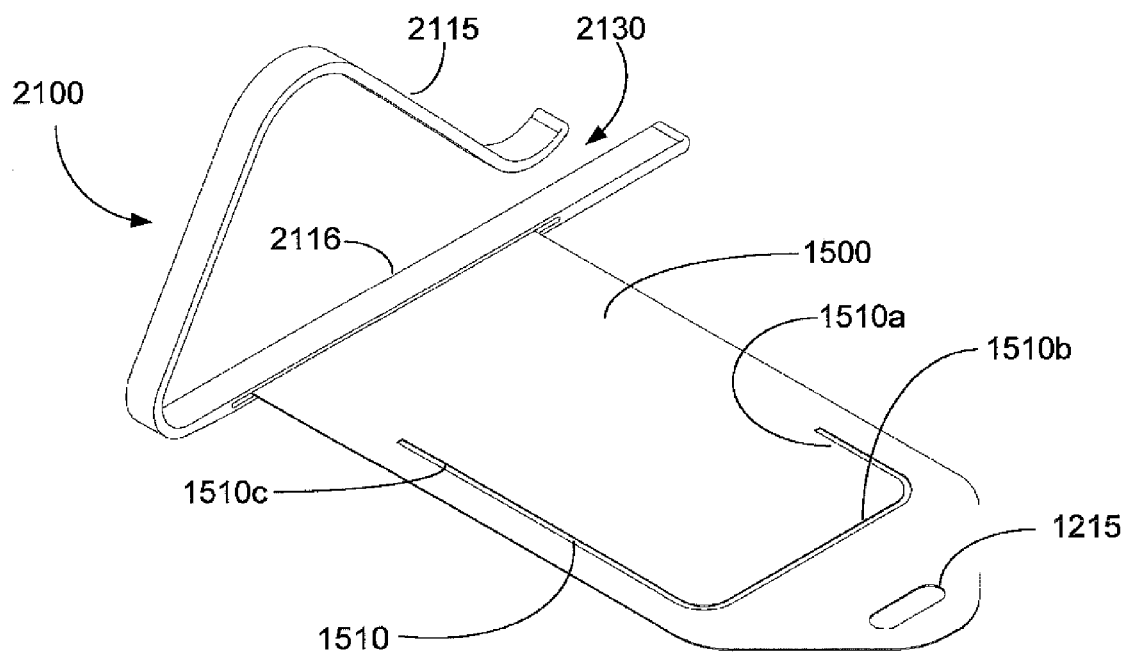
FIG. 5 shows an arrangement of a support member incorporating a cut-out portion in accordance with the present teaching.

FIG. 5 shows a further modification of the support member, in this exemplary arrangement optimised for use in retraction of the left lobe of the liver. In this arrangement the support member is again provided in the form of a mesh 1500, but in this arrangement is provided with a cut-out section 1510. In the exemplary utility of retraction of a liver, on location of the mesh under the liver and a subsequent lifting of the mesh, some of the liver mass falls through the hole created by the cut-out 1510. The mesh once pulled back to where it is anchored is effectively encircling the tip of the liver. The benefit of this approach is that it provides a mechanism for preventing the liver from slipping off the mesh. The exemplary cut-out 1510 shown in FIG. 5 comprises first 1510a, second 1510b and third 1510c cut out lines which perforate the integrity of the mesh fabric and are arranged with the first 1510a and third lines 1510c being coupled via the second line 1510b with the second line 1510b forming a base of the cut-out and being arranged substantially perpendicular to the longitudinal axis of the mesh. By having the longer cut out 1510c provided on the right hand side of the mesh—in the direction extending outwardly from the anchor 2100—the cut-out will provide a larger gap or aperture in this region for receiving the non-fixed edge of the left lobe. It will be observed from this exemplary arrangement that the cut-out is located in a region proximal to a tip of the mesh, in this arrangement adjacent to the eyelet 1215 that may be used to secure the mesh on effecting the retraction of the organ. The profile of the cut-out shown here is for illustrative purposes and it will be appreciated that it is not intended to limit the geometry of such a cut-out. This use of a cut-out could be combined with a drawstring which encircles the perimeter of the cut-out section and is used to provide lift to the mesh. The drawstring, if provided, would tighten the cut-out opening around the liver.

Figure 6:
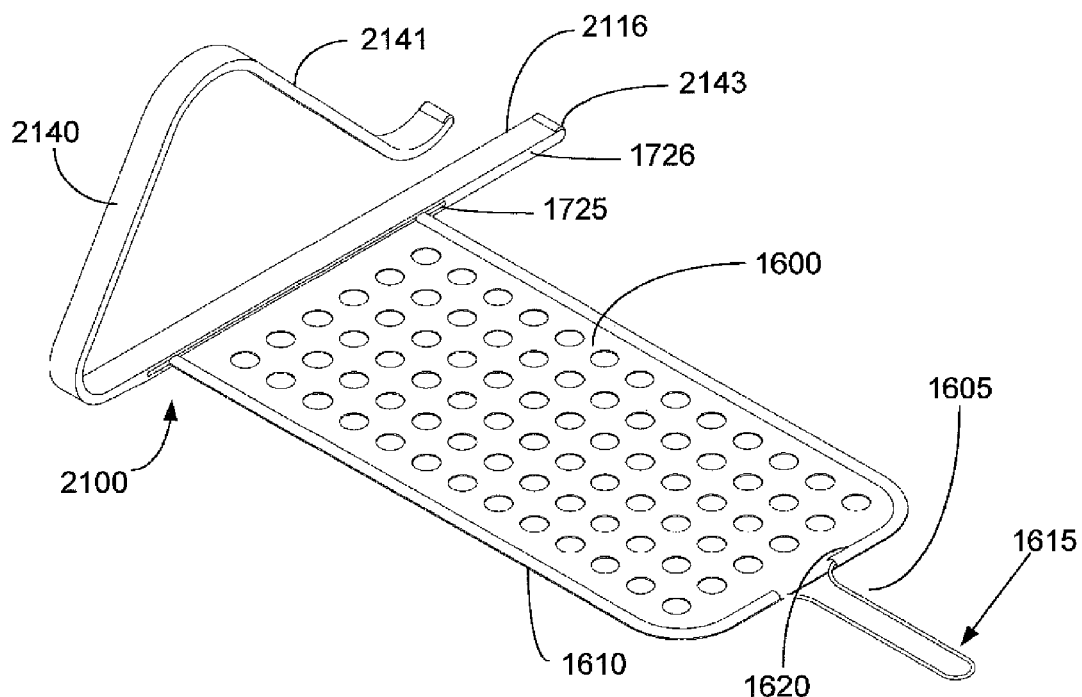
FIG. 6 shows the use of a drawstring about a perimeter of the support member in accordance with the present teaching.

In another configuration of a support member, shown in FIG. 6, the support member is again provided in the form of a mesh 1600, but in this arrangement a drawstring 1605 is provided about a perimeter 1610 of the mesh 1600. The drawstring 1605 may be provided within a channel 1620, such that it is encapsulated and will not snag against organs or the like during use. The function of the drawstring is to tighten the mesh 1600 about the organ being supported. The drawstring may have a hook/clip disposed on its end 1615 such that the drawstring once taut can be attached directly to the internal cavity of the abdomen. Alternatively, the drawstring could be taken external to the abdominal cavity through for example a trocar or needle with suture catching capability. An advantage of this approach over a mesh without a drawstring is that the organ is more securely held by the mesh and does not tend to slip out of the mesh, especially if the mesh is pulled back at an oblique angle relative to the anchor element—not shown. It will be appreciated that any one of a number of different attachment or coupling mechanisms could be used to effect a securing of the web to an internal portion of the anatomy at one or more locations including for example screws, hooks, sutures or the like.

It will be appreciated that in the exemplary arrangements described herein that it is possible to use the rigid nature of the abdominal wall—arising from inflation of the abdominal cavity during laparoscopic surgery to hang or suspend the weight of a lifted or otherwise moved organ therefrom. A retraction device such as that provided within the present teaching may be inserted wholly or fully into the internal cavity through an available trocar and then provided underneath organs or other visceral anatomy to move them from their normal location where they are occluding other target areas that require surgery. Such insertion of the devices will be effected by a surgeon or other member of the surgical team. The devices, once inserted are fully contained within the cavity and their manipulation is effected within the internal cavity. This allows the surgeon to locate them relative to the desired target organs—secure them in position and then conduct the necessary surgery without requiring subsequent manipulation or control of the devices externally of the body. In this way there is no need for additional surgical team members to hold or retain the retraction devices externally of the body cavity—as was a requirement of prior art arrangements or for steep patient positioning using gravity to move non target organs out of the field of view.

The support member is desirably configured so as to allow it to be expanded subsequent to insertion within the cavity. To allow for such expansion, it is desirable that the member is fabricated from a support material that would allow it to adopt a collapsed configuration during insertion into and removal from the body cavity. The support member is desirably formed of a material having a shape whose length is greater than its width. The material is arranged relative to the anchor so as to have a longitudinal axis substantially transverse to a longitudinal axis of the anchor 2100. The width of the support material will typically substantially correspond with the length of the anchor element. The support material may be formed as a mesh having a plurality of apertures or features relatively large in dimension (for example approximately 1 to 30 mm, or more desirably from 2-5 mm) formed on the contact surface thereof. These holes or features operably allow the organ tissue to invaginate into the material allowing for improved grip between the mesh and the organ tissue.

To couple the support member to the anchor a mouth region 1725 may be provided in one of the two jaws of the anchor. As shown in FIGS. 2 through 6, this is advantageously provided in the second jaw 2116, on a side face 1726 thereof. This side face 1726 is desirably orientated so as to be substantially perpendicular to a longitudinal axis of the support member. The mouth 1725 defines an opening for receipt of at least a portion of the support member therein.

By providing attachment of the support member 1200 (in FIG. 2) within an interior volume of the anchor, the pivot point of the support member relative to the anchor can be more precisely defined. Furthermore the level of securing of the two to one another can be improved.

The illustrated embodiments show the support member affixed into a recess in the lower arm. However, in further embodiments the support member may be bonded, or otherwise affixed to either the upper or lower surface of the lower arm, and be wrapped either clockwise or anticlockwise around the lower arm to effect a turning of the anchor element, which may be employed to improve the performance of the anchor.

Figure 7:
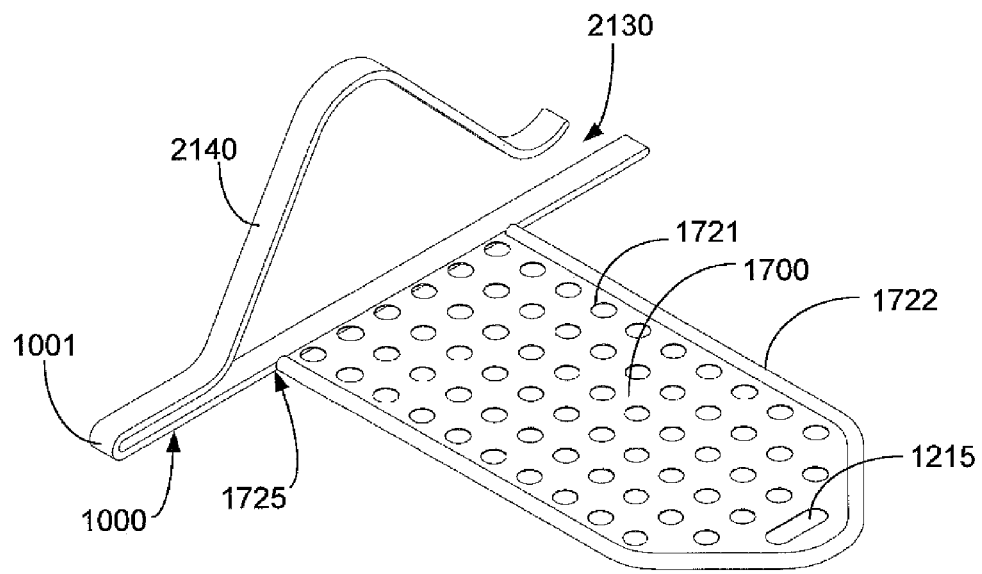
FIG. 7 shows a further arrangement of a retraction device in accordance with the present teaching.

As shown in FIG. 7, the support member 1700 may comprise a body portion 1721 of a first thickness and a ribbed perimeter portion 1722 of a second thickness, the second thickness being larger than the first thickness. By providing this ribbed element 1722 about the perimeter of the support member 1700, on an unfurling of the support member the ribbed element 1722 biases the remaining portion of the support member to adopt and maintain the expanded configuration. While this may be provided as a solid element, formed during for example the manufacturing process, it is also possible to provide such an arrangement through provision of an inflatable chamber about the perimeter of the device with inflation being effected post insertion into the abdominal cavity.

The support member may be provided with an adhesive surface to allow for its relative securing to at least one of the organs to be retracted or another anatomical feature to allow for the retracted organ to be retained in position.

Figure 8A:
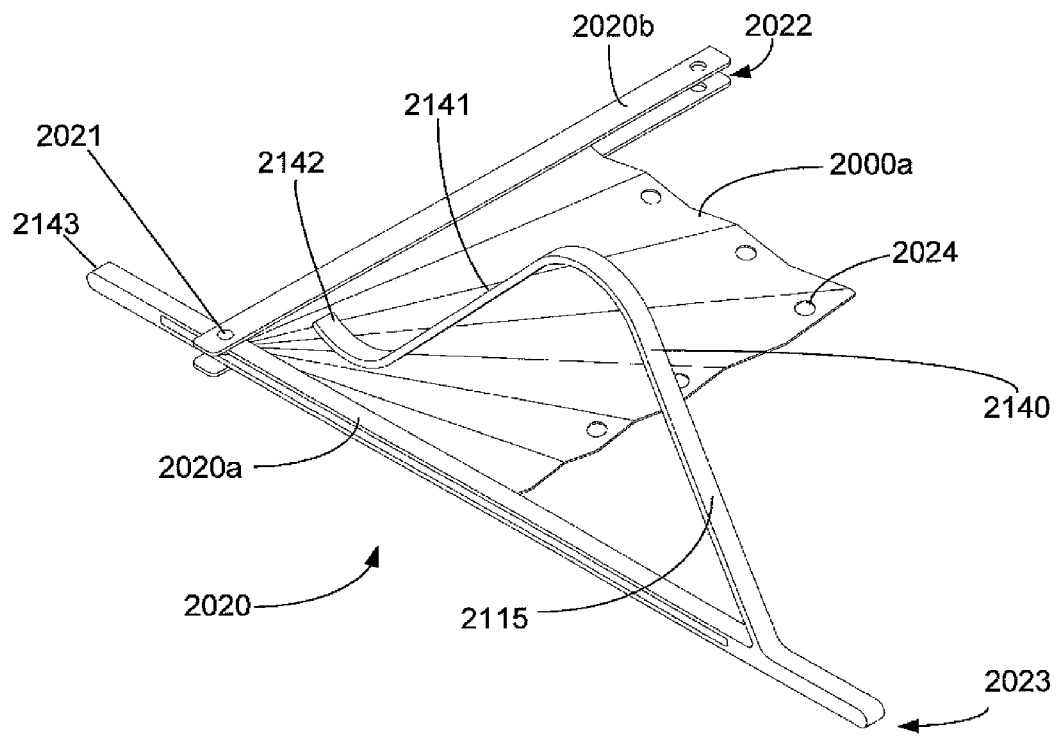
FIG. 8A shows a deployment arrangement for effecting extension of a support member in accordance with the present teaching.

FIG. 8A shows a further modification to a retraction device in accordance with the present teaching. In this arrangement, the anchor 2020 is provided in a two-part construction having a first 2020a and a second part 2020b. The second part 2020b is coupled to and pivotable relative to the first part 2020a via a pivot point 2021. The first part resembles the anchor element heretofore described and the same reference numerals are used for similar parts. The first and second parts are each coupled to the support member such that movement of the two parts effects a corresponding movement of the support member 2000a. During insertion of the device into the abdominal cavity, the first and second parts are axially aligned with one another by bringing an end 2022 of the second part towards a corresponding end 2023 of the first part. By moving these two ends towards one another the profile of the device is reduced and the support member 2000a is folded onto itself. The bringing together may be such as to have one of the two parts received into the other of the two parts. Once the device is provided through the trocar and into the abdominal cavity the first and second parts can be pivoted relative to one another. Desirably, the pivot point 2021 is provided proximal to the mouth portion of the anchor such that the second part 2020b may be pivotable away from the end 2023 of the first part 2020a. In this way, on presentation of the anchor under the organ to be supported, the leading edge 2143 of the first part 2020a will be presented initially under the organ. On suitable location of the first part 2020a, a pivoting of the second part 2020b can be effected by moving the end 2022 of the second part 2020b away from the first part 2020a. As each of first and second parts are coupled to the support member 2000a, their movement apart effects an opening of the support member in a fan-like arrangement. The provision of first and second parts provides two anchoring positions in two different planes. When used for retraction of a liver, such a configuration allows the user to encapsulate a portion of the organ within the first and second jaws of the first part 2020*a* and use the second part 2020*b* to provide increased support and ease of use in relation to deploying the support member under the liver. One or more suture couplings 2024 may be used to provide engagement points for a suture if required during the retraction process so as to enable an increase in tension or the like of specific portions of the support member 2000*a*.

Figure 8B:
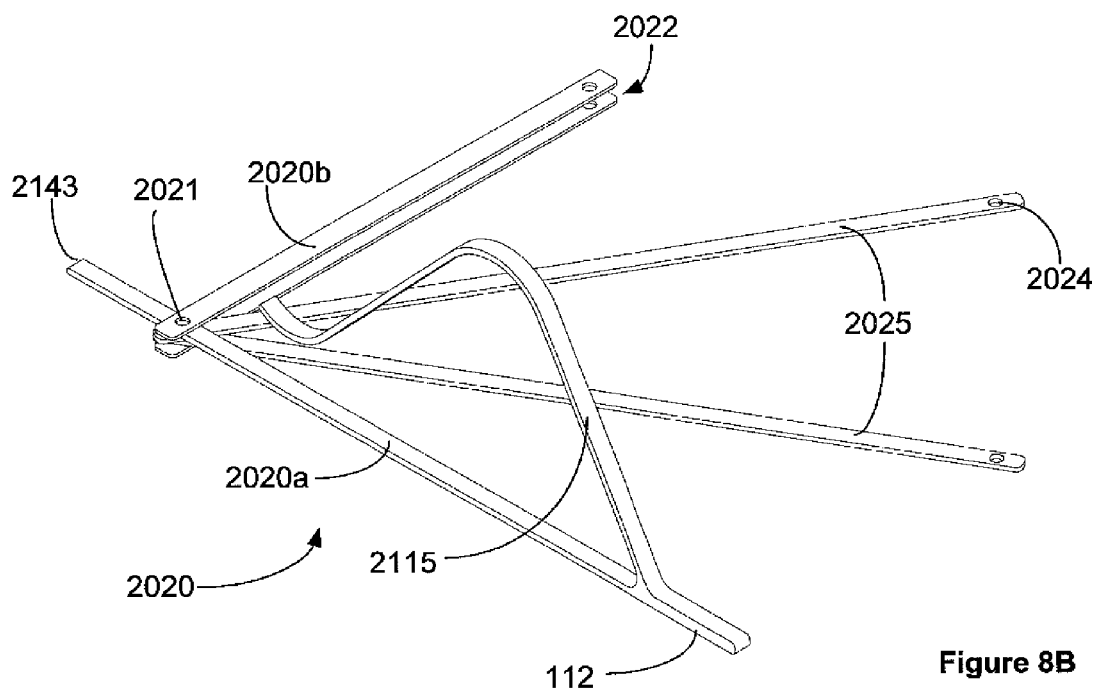
FIG. 8B shows another configuration of a fan-like arrangement in accordance with the present teaching.

FIG. 8B shows a modification to the arrangement of FIG. 8A whereas in contrast to the support member 2000*a* being formed from a single contiguous web or sheet, a plurality of individual fingers 2025 are provided. Each of the fingers 2025 are pivotable about the same pivot point 2021 as the second part 2020*b*. This pivoting may be achieved through a spring activation mechanism.

This device, similarly to previously described devices, is operably completely inserted through a trocar or single port MIS device. The leading edge 2143 is passed under the left liver and the sprung upper jaw 2115 is positioned on top of the left liver lobe. The device is then pushed onto the liver via the handle 112. The second part 2020*b* and each of the two illustrated fingers 2025 may then be withdrawn to the desired position required to effectively retract the organ. These supports may be configured to lock in 30 degree intervals so that when the second part 2020*b* is fully retracted to the 90 degree position, the first and second fingers 2025 are spaced 30 degrees apart as illustrated. A suture may then be tied through one of the suture holes 2024 and the device can then be fixed to a separate internal or external support. The device may be manufactured by lasing from nitinol sheet or the upper jaw 2115 may be formed from nitinol strip with each of the other components being of non shape memory metal or polymer construction. The individual fingers may also be connected via suture or wire or a flexible material may be positioned between each support member. It will be appreciated that while the fingers of this exemplary arrangement are not in the form of a web, they nevertheless each represent a support member as they must have sufficient strength to enable them to support the organ. This may further require each of the fingers to have a degree of flexibility to allow them to flex about the contours of the organ being supported.

Figure 9:
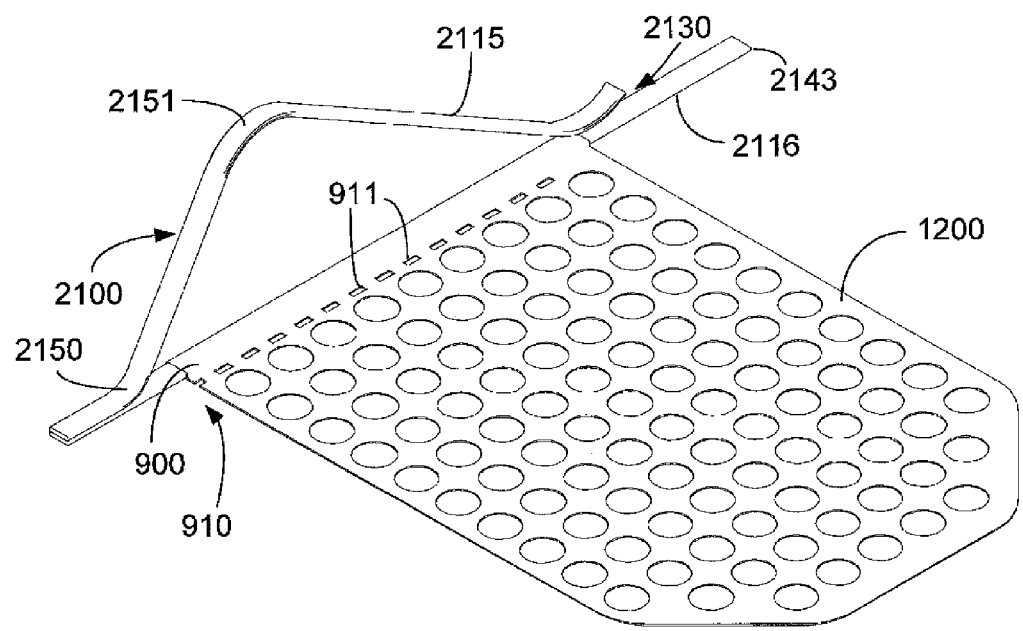
FIG. 9 shows another arrangement of a retraction device in accordance with the present teaching.
Figure 10:
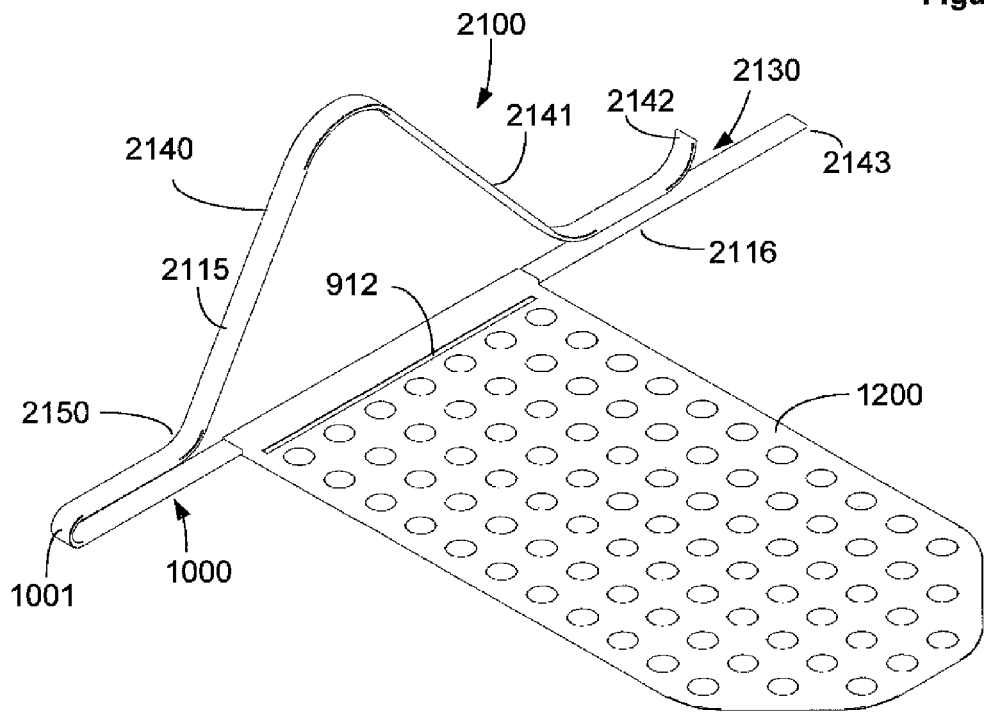
FIG. 10 shows a further arrangement of a retraction device in accordance with the present teaching.

FIGS. 9 and 10 show further modifications to a surgical retraction device in accordance with the present teaching. In these arrangements the same reference numerals are used for the same components. In FIGS. 9 and 10 the support member 1200 is coupled to the anchor element through a sleeve 900 defined in the support member. The second jaw 2116 of the anchor may be passed through the sleeve 900 so as to effect a relative securing of the anchor to the support member.

In these exemplary arrangements the support member 1200 is provided with a region of weakness 910 adjacent to its coupling to the anchor. In each exemplary arrangement, the line of weakness is provided substantially parallel with a longitudinal axis of the anchor. In FIG. 9, a plurality of individual perforations 911 are provided whereas FIG. 10 shows an alternative configuration having one extended cut out region 912. By removing portions of the material that form the fabric of the support member in this region of weakness, the structural integrity of the support member is weakened coincident with this region. Such a weakening at a predefined location will allow for a preferential tearing of the support member at this location. In this way the support member may be broken along this line to facilitate removal. In the arrangement of FIG. 10, a cutting of the cut-out from one side of the support member will not result in a complete separation of the support member relative to the anchor but rather allows the support member to rotate and be removed after the main anchor, during for example removal of the device through a trocar post operative use of the device. The anchor element of FIG. 10 is substantially similar to that described with reference to FIGS. 1A and 1B with a gap 1000 defined between the first and second jaws in the region between a first end 1001 of the anchor and the shoulder 2150. In contrast, FIG. 9 shows a configuration where the first and second jaws are in intimate contact with one another in this region. The two parts may be welded together or otherwise bonded. A sleeve may be place over the two at 1001 to assist with bonding or a hypotube may be placed over the same area and crimped to fix the two arms together. This arrangement allows the top and bottom components to be fabricated using two different materials.

Figure 11:
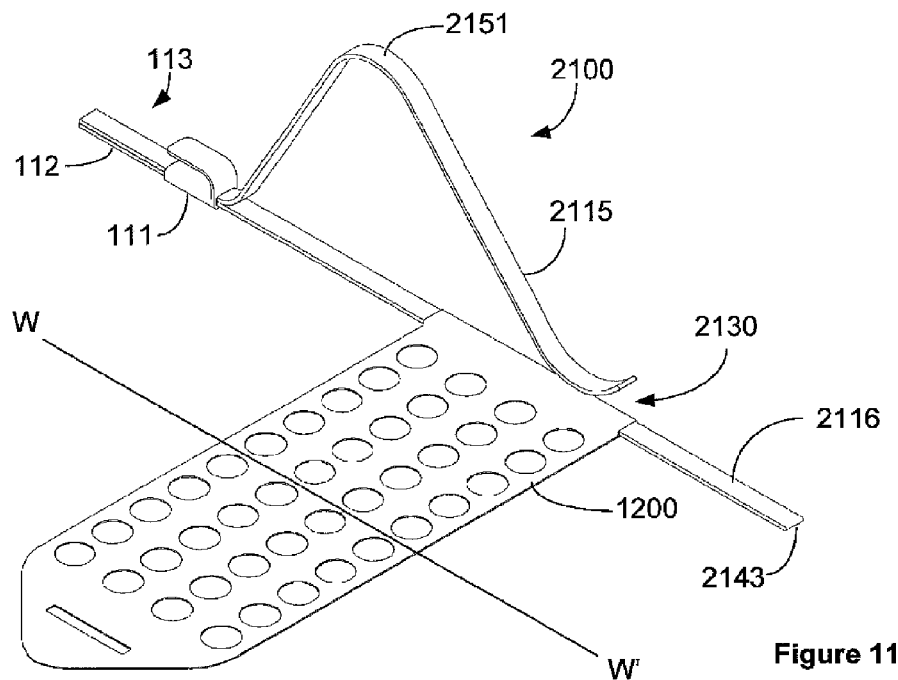
FIG. 11 shows a further arrangement of a retraction device in accordance with the present teaching.

FIG. 11 shows such a configuration where the upper jaw 2115 forming the top portion of the device may be fabricated from a shape memory material such as nitinol and the lower jaw 2116 portion which does not require shape memory functionality may be manufactured from a different metal or polymer. This configuration also allows for a higher compressive force to be achieved between the top and bottom portions.

The arrangement of FIG. 11 differs from previously described retraction devices in that it includes a slider 111 which is moveable along the longitudinal axis of the anchor 2100. A movement of the slider 111 towards the mouth 2130 effects a compression of the upper jaw 2115 downwardly towards the lower jaw 2116. It will be appreciated that the length of travel of the slider 111 is at least partially determined by the location of the support member 1200 relative to the anchor 2100. To this end, and to allow the slider to move at least coincident with the apex 2151 of the first jaw 2115, the web 1200 should be provided proximal to the mouth region 2130. As the slider 111 is moved towards the mouth 2130, the flexible nature of the upper jaw 2115 allows it to compress downwardly. By allowing the slider to travel past the apex 2151, complete compression of the upper jaw 2115 may be effected such that the upper jaw may be provided substantially parallel with the lower jaw 2116. This may be particularly advantageous in maintaining the anchor in a compressed state for transportation or storage purpose. It is also useful in maintaining the anchor in its compressed state during insertion or removal through a trocar or single port MIS device. By providing a moveable slider 111, it is also possible to control the level of compression exerted by the upper jaw 2115 downwardly to the lower jaw 2116, providing the surgeon with more flexibility as to the usage of the device.

In operation, the device may be completely inserted through a trocar or single port MIS device. The device would be provided with the slider 111 in an advanced position to allow for easy insertion, with the first and second jaws substantially parallel. In this arrangement, the support member 1200 may be folded under the upper arm 2115. After insertion into the abdominal cavity, the slider is retracted to the position such as shown in FIG. 11 to release the upper arm 2115 with a corresponding release of the support member 1200. The leading edge 2143 is then passed under the left liver and the upper arm 2115 is positioned on top of the left liver lobe. The device is then pushed onto the liver via a handle 112 provided on a body portion 113 of the anchor 2100. At this stage the slider can be advanced to tighten the grip of the upper arm 2115 on the liver tissue if required. When surgery is completed, the device is removed from the liver or target organ and the slider 111 may be fully advanced to again close the upper arm 2115 for device removal. As was discussed above, the upper 2115 and lower 2116 arm or just the upper 2115 arm may be manufactured from Nitinol or similar shape memory material to enable simple wrap down and expansion while the extendable support member 1200 may be formed as a mesh fabricated from for example a punched thin film extrusion/sheet or a woven mesh. In this exemplary configuration, the mesh features relatively large 2-10 mm holes to allow the organ tissue to invaginate into the support member.

Figure 12:
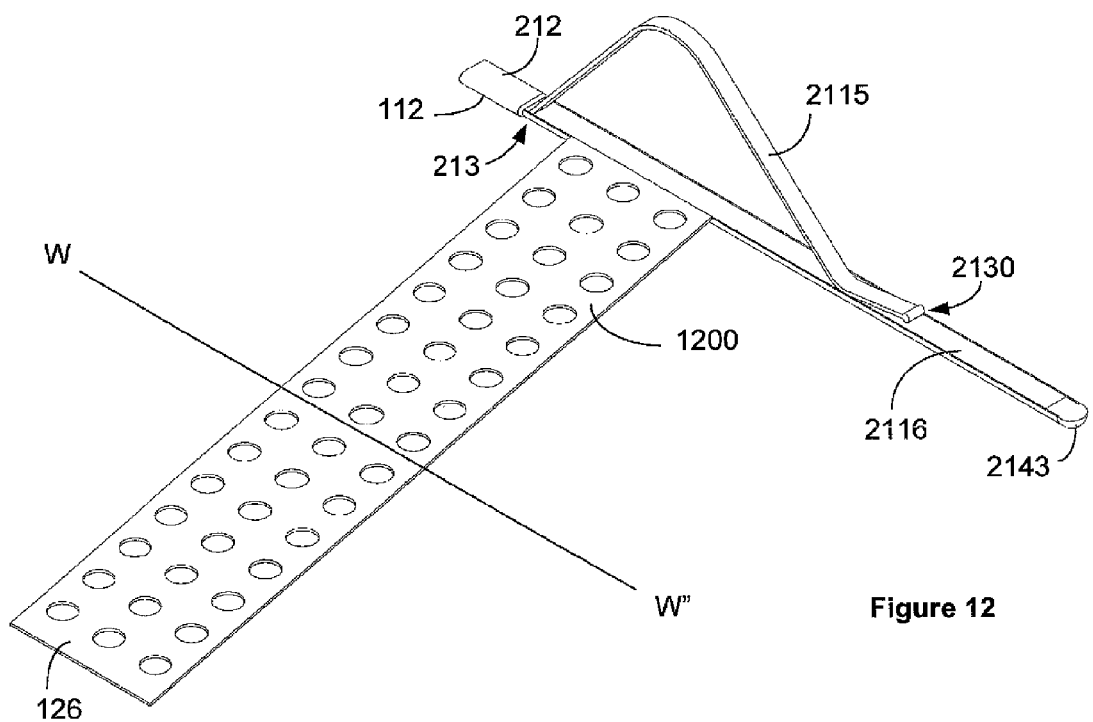
FIG. 12 shows a further arrangement of a retraction device in accordance with the present teaching.

The support member 1200 of this arrangement has dimensions across its width W-W' smaller than that described heretofore with regard to other arrangements. FIG. 12 shows a similar arrangement, where again the width along the line W-W" is reduced relative to the configurations of FIGS. 2-10. In this configuration, the end portion 126 of the support member 1200 is formed of a substantially straight edge. This is provided to illustrate that the dimensions and configuration of the support member 1200 is not intended to be limited to any one specific arrangement and that modifications can be made without departing from the teaching of the present invention. For example, while exemplary arrangements of coupling the support member to the anchor element have been described it will be appreciated that modifications to that heretofore described could include an arrangement whereby the support member extends obliquely and/or tapers outwardly from or inwardly to the anchor. Such an arrangement could be used in situations requiring shorter anchors relative to the width of the support member and/or could be used to bias the support member favourably relative to the anchor The arrangement of FIG. 12 also differs from that previously described in the nature of the coupling of the upper 2115 and lower 2116 arms to one another. In this arrangement, the device is constructed from an upper arm 2115, made from a Nitinol shape formed in flat wire and a lower arm 2116 made from a hypo tube. The hypo tube would be cut along its length with a whole section 212 left at the proximal end to form the handle 112. The Nitinol arm 2115 could then be passed through a mouth 213 formed in the whole section 212 of hypotube, which could then be crimped onto the Nitinol arm 2115. This crimped area of hypotube would form a handle or landing zone for a grasper used to manipulate the retractor device. An advantage of using a hypotube on the bottom is that the top arm would slide along and be retained within the hypo tube lumen as the device is wrapped down for delivery into the peritoneal cavity or for retrieval. A "U" shaped extrusion or moulding could also be used to achieve this advantage. The leading edge portion 2143 in this embodiment is a separate insert which slots into and is bonded to the lower arm. Such an arrangement may be advantageously employed in configurations where a wrapped down length of the upper arm is longer or shorter than that of the lower arm. Although not illustrated, the mesh may be wrapped so that is sits in the channel of the lower arm during delivery. In a moulded embodiment the whole lower arm detail may be formed in one part.

Figure 13:
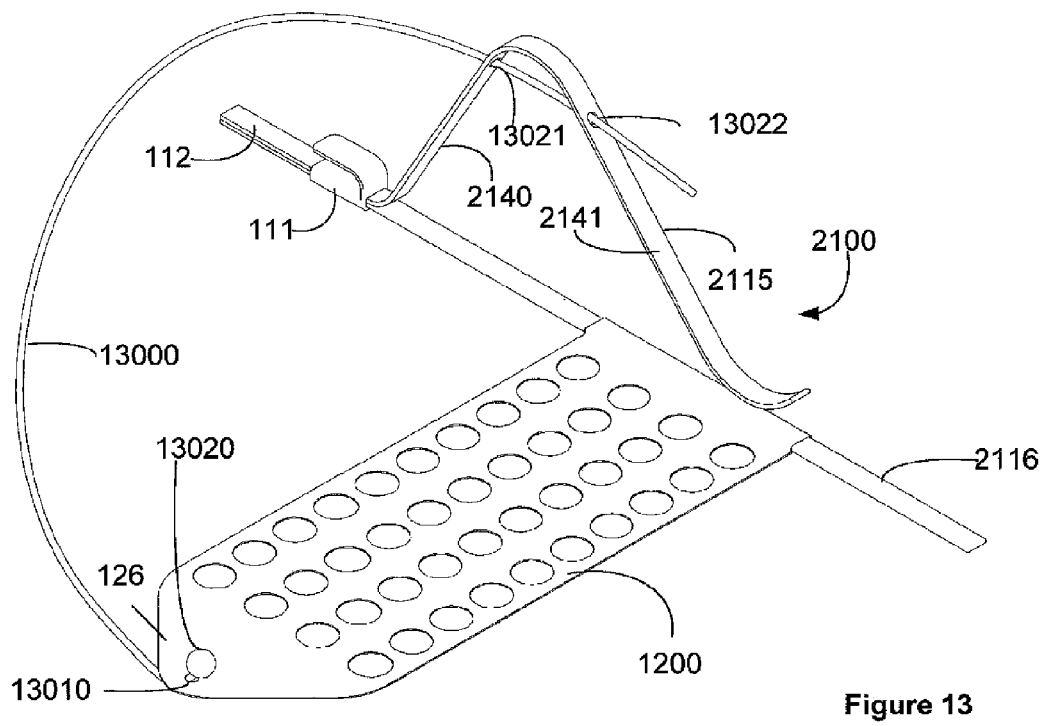
FIG. 13 shows another example of a retraction device in accordance with the present teaching.

FIG. 13 shows another example of a retraction device in accordance with the present teaching. In this arrangement the support member 1200 is coupled to a tether 13000 which in this exemplary arrangement is provided by a length of suture. It will be appreciated however that many other suitable materials could be utilized for this purpose. The tether is threaded through an aperture 13010 provided at an end region of the support member and is moveable within that aperture. One end of the tether 13000 is provided with a stop 13020 in the form of a bulbous element or knot whose dimensions are larger than that of the aperture and prevent the pulling of the tether through the aperture 13010.

The tether 13000 is also cooperable with the anchor element 2100. In this exemplary configuration first and second apertures that function in this embodiment as a cord lock 13021, 13022, are provided in the arms 2140, 2141 respectively. By engaging the tether with the anchor element 2100 and then increasing the tension on the tether, the end region 126 is retracted back towards the anchor element 2100 thereby, in use, enveloping any tissue within the support member 1200. By varying the tension on the tether, the level of retraction may be varied. Once the desired level is reached, then the tether may be secure relative to the anchor so as to retain that position.

It will be appreciated that there are many ways to vary the tension on the tether and it may be considered to use cord locks or the like which may be used to secure and tighten a tether or cord without the use of knots.

The use of a tether to achieve the relative securing of the support member to the anchor element is only one way of providing cooperation between the two components of the retraction device. For example using the configuration of FIG. 6, where the previously described drawstring may have a hook/clip disposed on its end 1615 such that the drawstring once taut can be attached directly to the internal cavity of the abdomen, in an arrangement such as that exemplified in FIG. 13 a hook or other engagement element could be provided on the anchor element which would be engageable with the drawstring to provide mutual inter-engagement. A further embodiment, not shown in the drawings, may include a support member coupled to a tether or anchor element which makes use of a hook and fastener coupling arrangement. An example of such a hook and fastener arrangement will be known to all as that sold under the VELCRO trademark. By coupling one of the hooks or fasteners to the support member 1200 and the other to an engagement surface, the positioning of the support member may be constrained. In one example the other of the hook or fastener is coupled to the anchor element. An advantage of such an arrangement is that the relative positioning of the support member may be easily modified by attachment and reattachment to the corresponding other of the hook or fastener.

Figure 14:
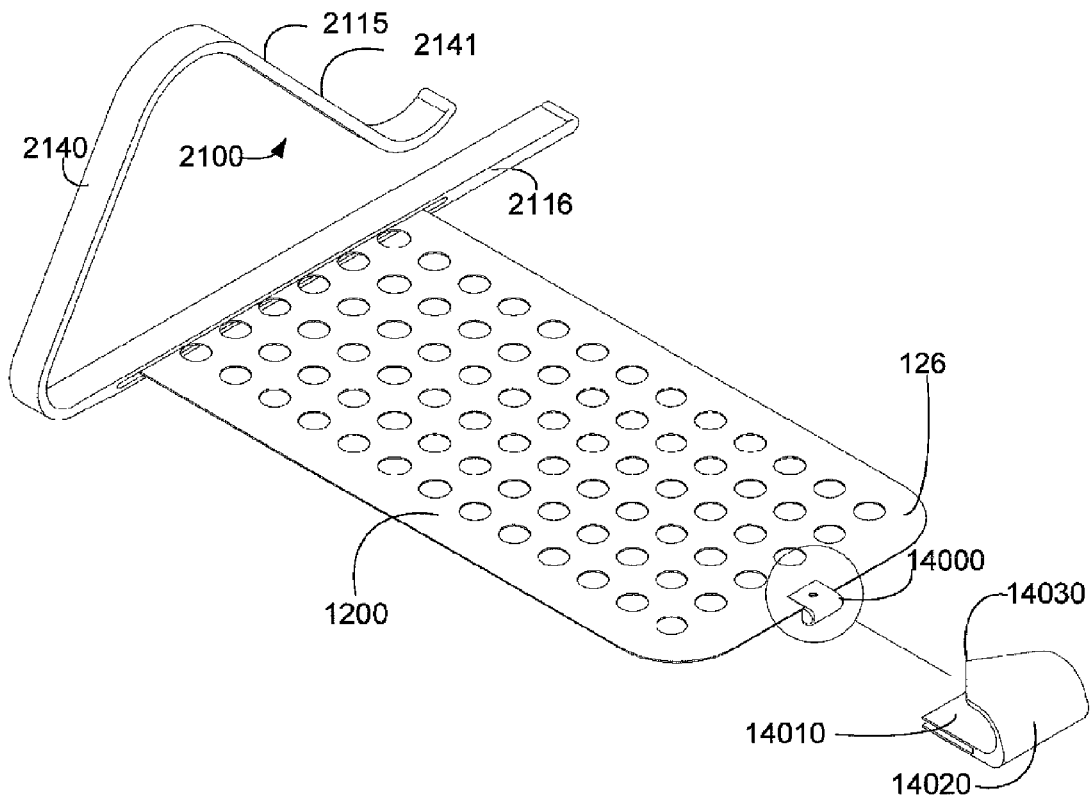
FIG. 14 shows another example of a retraction device in accordance with the present teaching.

In another configuration the other of the hook or fastener is provided as a separate element and in use is sutured to the inner abdominal wall using standard suturing technique. The support member can then be attached to the abdominal wall, and in doing so effect a lift of an organ. In a further embodiment, the hook and fastener arrangement could provide for attachment to the inner abdominal wall and would further include a muccal adhesive backing, which on contact with the inner abdominal wall affixes the hook and fastener strip. In yet another embodiment the support member could be fabricated from a material which is itself attachable directly to a corresponding material or surface It will be appreciated where hook and fasteners are provided as separate elements that the separate piece which is not coupled to the retraction element could be provided as a rolled up element which is passed through the trocar/cannula where it is then located as appropriate by the surgeon FIG. 14 shows another example of a retraction device in accordance with the present teaching. Again the same reference numerals will be used for similar components or elements to those described previously. In this arrangement a tether or anchor element 14000 is provided at an end region 126 of the support member. The anchor element 14000 has a planar surface 14010 and a curved portion 14020 which desirably terminates in a pointed surface

14030. The orientation of the pointed surface 14030 is shown in FIG. 14 as being directed rearwardly towards the anchor element 2100. In this arrangement when the support member 1200 is folded back upon itself, the pointed surface will be provided exposed above the now upper surface of the support element. This then allows the pointed surface to engage with a corresponding engagement surface. In one configuration this may be cooperation with one of the arms of the anchor element. In another configuration the engagement may be with the abdominal wall whereby the pointed surface is presented to and engages with the abdominal wall so as to hold the support member 1200 in place.

It will be appreciated that the anchor element 14000 resembles a needle and in this configuration the needle is riveted to the support member. As was detailed above, when the support member is reflected this curved needle could be hooked into the abdominal wall to hold the mesh of the support member in place. In another embodiment, this curved needle could be arrayed so that the whole underside of the edge of the support member is covered in needles. In such an embodiment the needles could all be connected to a flat strip, like teeth on a comb, this strip being then used to attach the needle to the support member.

Figure 15:
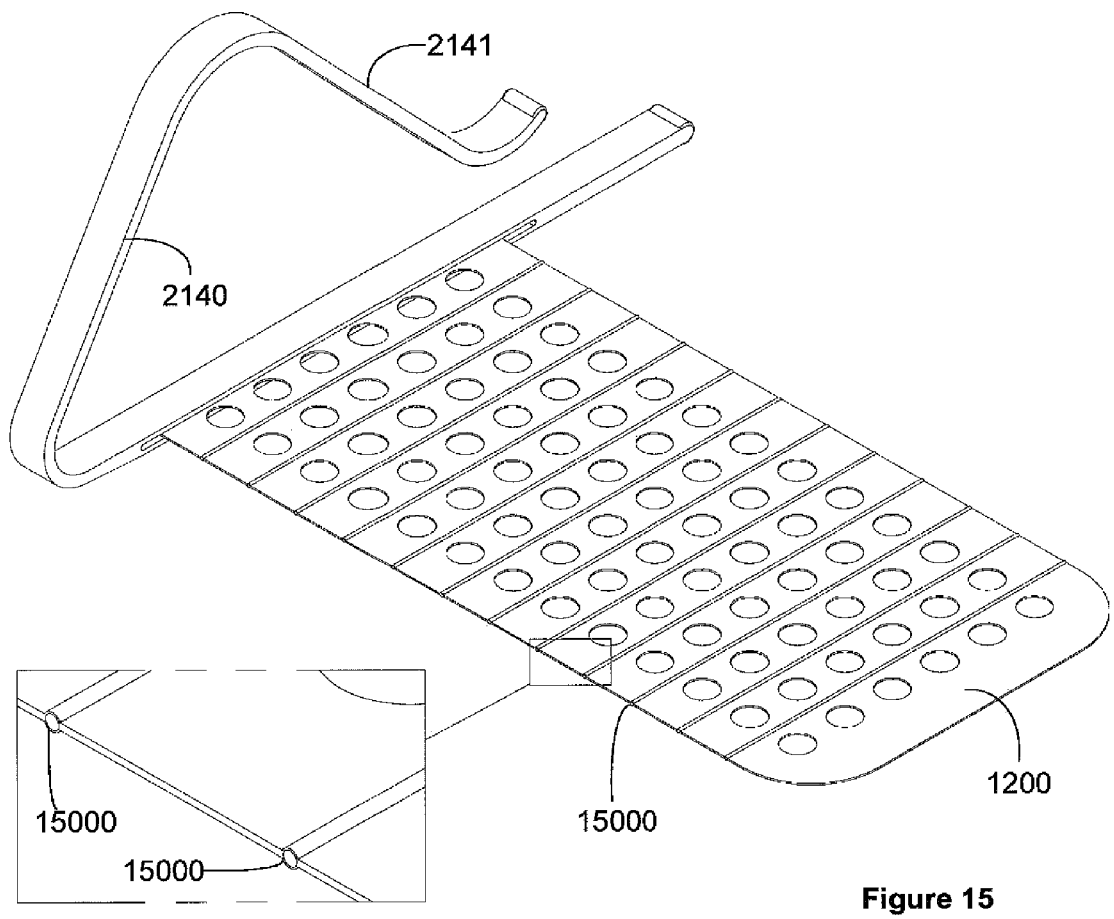
FIG. 15 shows another example of a retraction device in accordance with the present teaching.

FIG. 15 shows a further example of a retraction device in accordance with the present teaching. In this example, the support member 1200 is modified to provide one or more—in this exemplary arrangement a plurality—of needle storage slots 15000. Each of the slots 15000 resembles a rib extending transverse to the longitudinal axis of the support member 1200. The ribs provide a housing for a needle which may be located during laparoscopic delivery of the device into the patient. Once the anchor element and support member are in position, the needle may be removed from its slot. The needle-suture assembly is then useable in a securing of the support member 1200 in position by placing the needle through a point on the inner abdominal wall at which the support member is held taut. The needle-suture assembly may then be pulled through the abdominal wall and back down into the most appropriate needle slot i.e. the slot which enables the needle-suture assembly to hold the support member taut. The user may re-position the support member by moving the needle from one slot to another.

It will be appreciated that a retraction device such as this may also incorporate more than one suture-needle assembly. In a different configuration the needle-suture assembly could be used without needle storage slots. In this case, the needle-suture assembly could be 'tacked' into the edge of the support member 1200 for fixation.

It will be appreciated that a device as provided in accordance with the present teaching may have a number of requirements.

It should be capable of being inserted into a body cavity through available laparoscopic entry ports;

On insertion it should be capable of being located relative to and secured against an organ to be moved.

It should be capable of providing assisted lift or movement of that organ

It should be capable of being secured in place once that movement is achieved.

To provide the necessary lift it is desirable that the device has a contact surface that can be provided in contact with the organ to be lifted. Exemplary embodiments of a support member could be provided with high friction surfaces, adhesive coatings and the like. The support member may be provided from a low durometer tacky material, in the form of for example a web or mesh which has a sheet of non tack/low coefficient of friction material laminated on one side. This allows the mesh to be wrapped around itself for insertion into the abdominal cavity, wherein the lubricious side is outwardly facing. Once deployed, the tacky side of the mesh is that which will be in contact with the organ wherein the tacky surface provides better adhesion between the mesh and the organ being retracted. In any one of the configurations described the support member is desirably provided in a collapsed configuration which on receipt into the body cavity will be expanded to adopt the operational configuration. Such expansion could be effected using balloon technology or by a simple unfurling or other type of expansion of a collapsed sheet or web of material.

Once movement is achieved it is necessary to hold that organ in situ until the operation is complete. Two general exemplary types of means for securing the device in situ include in a first arrangement using a suture and needle to pull the flexible sheet taut. The suture may be either passed out through the abdominal wall and held in place through use of a washer type arrangement on the outer surface of the body wall which displaces the weight across a larger area or hold the suture in place internally using, for example, a self retaining mechanical screw fixed to the inner wall without passing right through the wall of the abdomen. Where the suture is held by the washer type arrangement, a suture holding feature could be incorporated into the washer comprising a tapered slot, or series of slots. It the case of using an internal screw, said screw may include an eyelet, through which suture passes. In this type of arrangement the suture pass through the eyelet and be attached to the support member or to a suture holding feature, as described above, which could be incorporated at any desirable position along the anchor element. In another embodiment there could be a detachable portion of mesh made from a bio-absorbable material like for example Polylactic Acid or Polyglycolide. This could be used in conjunction with a bio-absorbable screw, wherein at the end of the procedure a portion of the mesh is detached from the support member and left secured to the inside of the abdominal wall. In another technique a chemical bond may be used to adhere the device to an internal surface so as to hold the device in situ.

Additionally, the suture could be provided with features which make it compatible for use with a device which comprises of a support member coupled to an anchor element. For example the suture could be supplied with a needle on one end, this needle being either straight or curved. Disposed on the other end of the suture there could be a feature added which secures the suture to the support member, for example a ball. In use the suture would be threaded through the support member until the ball contacts, and is obstructed by, the support member. Such an example is similar to the knot 13020 described with reference to FIG. 13 whereby contact of the knot 13020 with the support member 1200 prevented further passage of the suture away from the support member.

It will be appreciated that the anchor element heretofore described provides for a capture and/or retention of an organ between two jaws of the anchor. The jaws are desirably displaced relative to one another to open a mouth of the organ for receipt of the organ. The mouth is desirably orientated to be substantially transverse to the longitudinal axis of the support member to which the anchor is coupled. In this way the anchor element is located relative to the organ substantially parallel to a pivot axis of the support member relative to the anchor element. While the exemplary arrangements have shown the anchor intimately contacting the support member it will be appreciated that modifications could be made to provide the anchor coupled to the support member through one or more support tethers. Furthermore whereas only one anchor has been described it will be appreciated that a plurality of anchors may be provided with individual ones of the anchors individually coupled to the support member. While preferred arrangements have been described in an effort to assist in an understanding of the teaching of the present invention it will be appreciated that it is not intended to limit the present teaching to that described and modifications can be made without departing from the scope of the invention.

It will be appreciated that the exemplary arrangements or examples of devices have been described with reference to the Figures attached hereto. Where a feature or element is described with reference to one Figure, it will be understood that the feature or element could be used with or interchanged for features or elements described with reference to another Figure or example. The person of skill in the art, when reviewing the present teaching, will understand that it is not intended to limit the present teaching to the specifics of the illustrated exemplary arrangements as modifications can be made without departing from the scope of the present teaching.

The words comprises/comprising when used in this specification are to specify the presence of stated features, integers, steps or components but does not preclude the presence or addition of one or more other features, integers, steps, components or groups thereof.

The invention claimed is:

1. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
wherein in the operational configuration the anchor element provides for an internal anchoring of the device at a predetermined position within the abdominal cavity and the support member is moveable about the anchor element to contact with and lift a desired organ to a retracted position and wherein the support member is furled or rolled to adopt the insertion configuration, wherein in the operational configuration the expansion of the device is effected by unfurling the support member to an extended configuration for contact with the desired organ so as to achieve the necessary lift of that organ and wherein the device includes an air inlet and balloon to provide for assisting in expansion of the support member.

2. The device of claim 1 wherein in the operational configuration the support member is expanded and deployed to provide for the lift of desired organs so as to allow surgical access to other organs below.

3. The device of claim 1 wherein a first jaw of the anchor element is dimensioned to be receivable below a predetermined anatomical feature, where once inserted, the weight of one or more organs acting on the anchor will retain the anchor in situ providing for an internal anchoring of the device within the abdominal cavity.

4. The device of claim 3 wherein configured such that on receipt of the first jaw below the predetermined anatomical feature, the second jaw is disposed above the anatomical feature thereby securing the anatomical feature between the first and second jaws.

5. The device of claim 1 wherein the diameter of the anchor element is less than 1.0 cm in the collapsed configuration, to allow for its presentation through a trocar or cannula into the abdominal cavity.

6. The device of claim 1 wherein the support member may be furled about or within the anchor element so as to reduce the diameter of the device in its insertion configuration.

7. The device of claim 1 wherein the support member comprises a contact surface which operationally is in contact with the desired organ.

8. The device of claim 7 wherein the support member is flexible to allow the contact surface to adopt the contours of the organ it is in contact with.

9. The device of claim 1 wherein the anchor is coupled to the support member through one or more support tethers.

10. The device of claim 9 comprising a plurality of anchors individually coupled to the support member.

11. The device of claim 1 wherein the support member is dimensioned to envelop a lower portion of an organ at two sides thereof so as to operably effect a lift of that organ out of the field of view of a surgeon.

12. The device of claim 11 wherein the support member comprises a first and second contact location for securing the support member during an adoption of the operational configuration, and wherein on adoption of the operational configuration the organ is operably disposed between each of the first and second contact location.

13. The device of claim 1 wherein the anchor element is fabricated at least in part from a shape memory material.

14. The device of claim 13 wherein a first or second jaw of the anchor element is fabricated from a shape memory material.

15. The device of claim 13 wherein a first and second jaw of the anchor element are fabricated from a shape memory material.

16. The device of claim 1 wherein the support member comprises a cut-out portion within which at least a portion of a retracted organ may pass through.

17. The device of claim 1 comprising a drawstring provided in co-operation with the support member, an application of tension to the drawstring effecting a corresponding change in shape of the support member.

18. The device of claim 17 wherein the drawstring is operable to effect a contraction of the support member about a retracted organ.

19. The device of claim 1 wherein at least a portion of the support member is receivable into an interior volume of the anchor element.

20. The device of claim 1 wherein at least one of the jaws is pivotable relative to the other of the jaws to allow for movement of the jaws away from one another to facilitate the presentation of an organ into the mouth of the anchor element.

21. The device of claim 20 configured to co-operate with an external device so as to allow for provision of an external force so as to effect a separation of the jaws away from one another.

22. The device of claim 1 wherein the anchor element further comprises a body portion coupled or integrally formed with at least one of the jaws.

23. The device of claim 22 wherein the body portion extends distally away from the mouth of the anchor element.

24. The device of claim 22 wherein the body portion provides a coupling contact for effecting a securing of the anchor element at a desired position within the abdominal cavity.

25. The device of claim 22 wherein the body portion extends longitudinally away from the jaws.

26. The device of claim 1 comprising at least one coupling surface configured to cooperate with a separate coupling tool.

27. The device of claim 1 wherein the first and second jaws of the anchor element are integrally formed with one another and are fabricated in a shape memory material such that the device may deform on actuation of a force thereon but returns to its normal state on removal of said force.

28. The device of claim 27 wherein the jaws are spaced apart from another, a first jaw comprising a kink, the kink effecting a biasing of the first jaw towards the lower jaw such that the jaws are naturally biased towards one another.

29. The device of claim 27 wherein the jaws are operably separable to allow for the location of an organ or other tissue therebetween.

30. The device of claim 1 comprising a slider, the slider being moveable along the anchor element to effect a closure of the jaws.

31. The device of claim 1 comprising means for coupling with a suture or other fastening means to effect a movement of the clasped organ or tissue from its normal resting position to an operational site.

32. The device of claim 1 wherein the first segment is angularly offset from the second jaw by an acute interior angle.

33. The device of claim 1 wherein the first segment is angularly offset from the second segment by an acute interior angle.

34. The device of claim 1 wherein at least one of the first and second jaws comprise teeth.

35. The device of claim 34 wherein each of the first and second jaws comprise teeth, the teeth being provided relative to one another to at least partially overlap.

36. The device of claim 1 wherein the second jaw extends further than the first jaw, such that on operable presentation of the device to an organ or tissue, the second jaw will abut against the organ or tissue prior to the first jaw.

37. The device of claim 1 wherein the jaws are biased towards one another to so as to normally adopt a closed or pre-determined configuration.

38. Use of a device as claimed in claim 1 for laparoscopic colon or large bowel procedures.

39. Use of a device as claimed in claim 1 for providing for surgical movement of the small bowel.

40. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
   a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
   wherein in the operational configuration the anchor element provides for an internal anchoring of the device at a predetermined position within the abdominal cavity and the support member is moveable about the anchor element to contact with and lift a desired organ to a retracted position, the device further comprising a shape memory material and wherein the shape memory material contacts the support member such that on adoption of the operational configuration biases the support member to adopt an expanded configuration, and wherein the shape memory material comprises a plurality of distinct elements arranged as ribs within the support member.

41. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
   a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
   wherein in the operational configuration the anchor element provides for an internal anchoring of the device at a predetermined position within the abdominal cavity and the support member is moveable about the anchor element to contact with and lift a desired organ to a retracted position and wherein the first segment extends away from the second jaw and the second segments extends towards the second jaw.

42. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
   a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
   wherein in the operational configuration the anchor element provides for an internal anchoring of the device at a predetermined position within the abdominal cavity and the support member is moveable about the anchor element to contact with and lift a desired organ to a retracted position and wherein the first jaw comprises a third segment, provided at an end portion of the second segment, the third portion defining an atraumatic tip of the first jaw.

43. The device of claim 42 wherein the third segment comprises a planar portion extending from the second segment, the planar portion being substantially parallel with the second jaw.

44. The device of claim 42 wherein the third segment comprises a curved surface, the curved surface defining the end of the first jaw, the planar portion being provided between the curved surface and the second segment.

45. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
  a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
  wherein in the operational configuration the anchor element provides for an internal anchoring of the device at a predetermined position within the abdominal cavity and the support member is moveable about the anchor element to contact with and lift a desired organ to a retracted position and wherein the first and second segments of the first jaw and a portion of the second jaw are arranged relative to one another to define an acute triangle.

46. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
  a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
  wherein in the operational configuration the anchor element provides for an internal anchoring of the device at a predetermined position within the abdominal cavity and the support member is moveable about the anchor element to contact with and lift a desired organ to a retracted position and wherein the support member comprises a web of material, the web of material having a region of weakness adjacent to its coupling to the anchor, the region of weakness operably providing a preferential separation of the web from the anchor in a location adjacent to the region of weakness.

47. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:
  a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and
  wherein in the operational configuration the anchor element provides for an internal anchoring of the device at a predetermined position within the abdominal cavity and the support member is moveable about the anchor element to contact with and lift a desired organ to a retracted position and wherein the support member coupled to the anchor element at a first location and may be pivoted about that first location to secure a body organ or tissue within the support member.

48. The device of claim 47 configured to provide a coupling of the support member to the anchor element at a second location.

49. The device of claim 47 wherein the support member is cooperable with a tether, movement of the tether providing a corresponding movement of the support member.

50. The device of claim 49 wherein the tether is cooperable with the anchor element to achieve a securing of the support member relative to the anchor element.

51. The device of claim 49 wherein the tether is configured to engage with and attach to an abdominal wall to achieve a securing of the support member relative to the abdominal wall.

52. The device of claim 49 wherein the tether comprises a needle receivable within at least a portion of the support member.

53. A method of moving an organ or tissue within an abdominal cavity during laparoscopic surgery, the method comprising:
  a) providing a laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and wherein in the operational configuration the anchor element provides for an internal anchoring of the device at a predetermined position within the abdominal cavity and the support member is moveable about the anchor element to contact with and lift a desired organ to a retracted position and;
  b) disposing that device through a trocar or cannula into the abdominal cavity;
  c) placing a leading edge under the organ/tissue being retracted;
  d) biasing the jaws open to receive the organ or tissue using, for example, a laparoscopic grasper or forceps, and then removing the biasing force such that the jaws grasp the organ or tissue within the mouth of the device;
  e) moving the device to effect a corresponding movement of the grasped organ or tissue;
  f) fixing the device internally or externally to maintain retraction; and
  g) unfixing and removing the device from the inner abdominal cavity.

54. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:

a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and wherein in the operational configuration the anchor element provides for an internal anchoring of the device at a predetermined position within the abdominal cavity and the support member is moveable about the anchor element to contact with and lift a desired organ to a retracted position, the device further comprising at least one finger pivotably coupled to the anchor element, and wherein at least one finger is pivotably coupled to the anchor element in a region proximal to the mouth of the anchor element.

55. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:

a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, a plurality of fingers pivotably coupled to the anchor element, individual ones of the fingers being pivotable through different amounts to others of the fingers, and wherein in the operational configuration the anchor element provides for an internal anchoring of the device at a predetermined position within the abdominal cavity and the support member is moveable about the anchor element to contact with and lift a desired organ to a retracted position, the device further comprising at least one finger pivotably coupled to the anchor element.

56. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:

a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and wherein in the operational configuration the anchor element provides for an internal anchoring of the device at a predetermined position within the abdominal cavity and the support member is moveable about the anchor element to contact with and lift a desired organ to a retracted position, the device further comprising at least one finger pivotably coupled to the anchor element, and wherein at least one finger defines the support member.

57. A laparoscopic surgical retraction device having an insertion configuration and an operational configuration wherein in the insertion configuration the device is collapsible such that the dimensions of the device can be reduced so as to allow the complete insertion of the device through a trocar or cannula into an internal abdominal cavity wherein it may be expanded to adopt the operational configuration; the device comprising:

a support member coupled to an anchor element, the anchor element comprising a pair of jaws defining a mouth within which at least a portion of an organ or tissue may be grasped, the jaws being biased towards one another, and wherein a first jaw comprises a first and a second segment angularly offset from one another, and wherein in the operational configuration the anchor element provides for an internal anchoring of the device at a predetermined position within the abdominal cavity and the support member is moveable about the anchor element to contact with and lift a desired organ to a retracted position, the device further comprising at least one finger pivotably coupled to the anchor element, and wherein the support member comprises a web of material, at least one finger being coupled to the web, a pivoting of at least one finger effecting an extension of the web relative to the anchor element.

* * * * *